United States Patent [19]

Blum et al.

[11] 4,069,246

[45] Jan. 17, 1978

[54] PRODUCTION OF 1-HYDROXY-ALKANE-1,1-DIPHOSPHONIC ACIDS

[75] Inventors: Helmut Blum; Karl-Heinz Worms, both of Dusseldorf-Holthausen, Germany

[73] Assignee: Henkel Kommanditgesellschaft auf Aktien, Dusseldorf, Germany

[21] Appl. No.: 692,326

[22] Filed: June 3, 1976

Related U.S. Application Data

[63] Continuation-in-part of Ser. No. 525,156, Nov. 19, 1974, abandoned, which is a continuation of Ser. No. 317,663, Dec. 22, 1972, abandoned.

[30] Foreign Application Priority Data

Dec. 31, 1971  Germany ............................. 2165833

[51] Int. Cl.$^2$ ............................................. C07F 9/38
[52] U.S. Cl. ............................................. 260/502.4 P
[58] Field of Search ................................. 260/502.4 P

[56] References Cited

U.S. PATENT DOCUMENTS 3,214,454  10/1965  Blazer et al. ................. 200/502.4 A

FOREIGN PATENT DOCUMENTS 1,002,355  2/1957  Germany .......................... 260/502.5

OTHER PUBLICATIONS

Whitmore et al., "J. Am. Chem. Soc.", vol. 54, (1932), pp. 3441–3447.
Whitmore et al., "J. Am. Chem. Soc.", vol. 63, (1941), pp. 1118–1120.
Gray, "The Chemistry of Dinitrogen Tetroxide", 1958, p. 16.

*Primary Examiner*—Joseph E. Evans
*Attorney, Agent, or Firm*—Hammond & Littell

[57] ABSTRACT

A process for the production of 1-hydroxy-alkane-1,1-diphosphonic acids comprises reacting 1-amino-alkane-1,1-diphosphonic acids with nitrous acid, halides of nitrous acid or a substance forming nitrous acid under the reaction conditions.

8 Claims, No Drawings

PRODUCTION OF 1-HYDROXY-ALKANE-1,1-DIPHOSPHONIC ACIDS

REFERENCE TO PRIOR APPLICATION

This application is a continuation-in-part of Ser. No. 525,156, filed Nov. 19, 1974, and now abandoned, which application was a continuation of Ser. No. 317,663, filed Dec. 22, 1972, and now abandoned.

PRIOR ART

A number of syntheses are already known for the production of 1-hydroxy-alkane-1,1-diphosphonic acids. The best known methods consist in reacting acylating agents, particularly carboxylic acid chlorides or carboxylic acid anhydrides or mixture thereof, with phosphoric acid. It is also possible to react phosphorus trihalides with carboxylic acids to produce 1-hydroxy-alkane-1,1-diphosphonic acids. The resulting products are not homogeneous, however. For the production of pure substances it is therefore necessary to effect cumbersome purifying operations. It is furthermore known to subject the crude products to a steam treatment for the production of homogeneous products and to obtain in this manner 1-hydroxy-alkane-1,1-diphosphonic acids in good yields. The method of steam treatment is frequently very time-consuming and expensive especially in technical production, particularly when higher carboxylic acids, such as capronic acid, benzoic acid and similar compounds must be eliminated.

OBJECTS OF THE INVENTION

It is an object of the present invention to provide a process for the preparation of 1-hydroxy-alkane-1,1-diphosphonic acid of the formula

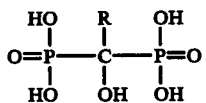

wherein R is a member having from 1 to 12 carbon atoms selected from the group consisting of alkyl having 1 to 6 carbon atoms, cyclohexyl, phenyl and phenylalkyl, all having substituents selected from the group consisting of hydrogen, methyl, ethyl, methoxy, ethoxy, and halogen, consisting essentially of reacting the corresponding 1-amino-alkane-1,1-diphosphonic acid of the formula

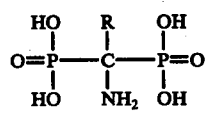

in which R has the above-assigned meaning, with at least the stoichiometric amount calculated as nitrous acid, of an aqueous acid compound selected from the group consisting essentially of (a) nitrous acid, (b) halides of nitrous acid, and (c) substances forming nitrous acid under the reaction conditions, at a temperature between 0° and 50° C; and recovering said 1-hydroxy-alkane-1,1-diphosphonic acid.

Other and further objects of the present invention will become apparent as the description thereof proceeds.

DESCRIPTION OF THE INVENTION

The present invention provides a process for the preparation of 1-hydroxy-alkane-1,1-diphosphonic acid of the formula

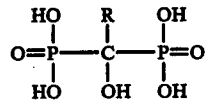

wherein R is a member having from 1 to 12 carbon atoms selected from the group consisting of alkyl having 1 to 6 carbon atoms, cyclohexyl, phenyl and phenylalkyl, all having substituents selected from the group consisting of hydrogen, methyl, ethyl, methoxy, ethoxy, and halogen, consisting essentially of reacting the corresponding 1-amino-alkane-1,1-diphosphonic acid of the formula

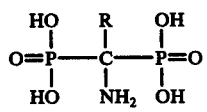

in which R has the above-assigned meaning, with at least the stoichiometric amount calculated as nitrous acid, of an aqueous acid compound selected from the group consisting essentially of (a) nitrous acid, (b) halides of nitrous acid, and (c) substances forming nitrous acid under the reaction conditions, at a temperature between 0° and 50° C; and recovering said 1-hydroxy-alkane-1,1-diphosphonic acid.

As stated above, R is a member having from 1 to 12 carbon atoms which can be aliphatic, such as alkyl of 1 to 6 carbon atoms or cyclohexyl, or aromatic such as phenyl or alkylphenyl, for example benzyl. There may be substituents which do not react with nitric acid bonded to the R group. Examples of these substituents include hydrogen, lower alkyl such as methyl or ethyl, lower alkoxy such as methoxy or ethoxy or halogen. In each case, the total number of carbon atoms does not exceed 12. The 1-amino-alkane-1,1-diphosphonic acids are known compounds. They can be produced, for example, by reacting corresponding monocarboxylic amides with $PCl_3$ and subsequently hydrolyzing the reaction product. The reaction can also be effected by adding phosphoric acid. Other methods for producing the starting materials are disclosed in copending U.S. application Ser. No. 184,635 filed Sept. 28, 1971, now abandoned, Ser. No. 184,622 filed Sept. 28, 1971, now abandoned and Ser. No. 235,383 filed Mar. 16, 1972, now U.S. Pat. No. 4,006,182.

The process of the present invention is generally carried out at temperatures ranging from 0° to 50° C, preferably at 10° C to 45° C. Accordingly, the process can be carried out by reacting aqueous solutions or aqueous suspensions of the corresponding 1-amino-alkane-1,1-diphosphonic acids with nitrous acid. The nitrous acid can be formed by introducing into the aqueous media suitable nitrogen oxides, such as $NO_2$ or $N_2O_4$, or particularly $N_2O_3$. If necessary, corresponding technical waste gases containing these nitrogen oxides can be used. Also the necessary nitrous acid can be produced in the aqueous solution by reacting nitrites with mineral acids. Another method of forming nitrous acid comprises adding an alkali metal nitrate solution slowly to an acid solution.

In order to obtain a complete reaction, at least a stoichiometric amount of the acid compound calculated as nitrous acid should be used. In some cases, however, a certain excess is used, preferably from 1.2 to 2 times the molar amount of the acid compound calculated as nitrous acid is used. It is also advisable to slowly add the nitrous acid or the substances forming nitrous acid to the aqueous solution or suspension of the amino compound.

Instead of utilizing nitrogen oxides, nitrosyl chloride can be used.

The advantages of the new method include the direct production of 1-hydroxy-alkane-1,1-diphosphonic acids, as pure and homogenous products, by utilizing the readily available 1-amino-alkane-1,1-diphosphonic acids as a starting material. The frequently expensive, subsequent purifying operation, which was necessary heretofore to obtain pure and homogeneous products, is thusly eliminated.

The following examples are merely illustrative of the present invention without being deemed limitative in any manner thereof.

EXAMPLE 1

$N_2O_3$ is slowly added, while stirring, into a 2% aqueous solution of 1-amino-ethane-1,1-diphosphonic acid at 10° C. The amount of $N_2O_3$, calculated as nitrous acid, is about 1.5 times the stoichiometrically required amount. Subsequently the solution is concentrated in a vacuum evaporator and 1-hydroxy-ethane-1,1-diphosphonic acid is separated in the form of the hydrate. The yield is almost 100%.

EXAMPLE 2

125 m moles of 1-amino-butane-1,1-diphosphonic acid are dissolved or suspended in 2 liters of water. Subsequently the solution is cooled to 10° C and $N_2O_3$ is slowly introduced. After about 5 hours no starting material can be detected any longer in the reaction mixture by chromatography. Then the reaction mixture is concentrated in a vacuum evaporator to 150 cc and adjusted with concentrated sodium hydroxide to a pH value of 12. By adding ethyl alcohol, 1-hydroxy-butane-1,1-diphosphonc acid is precipitated in the hydrate form of the sodium salt having 17 $H_2O$. The yield is 85%.

EXAMPLE 3

125 m mols of 1-amino-benzyl-1,1-diphosphonic acid are dissolved in 4 liters of water. Then $N_2O_3$ is introduced at about 20° C until the starting material can no longer be detected by chromatography. Subsequently the reaction mixture is concentrated in a vacuum evaporator. After prolonged standing, the 1-hydroxy-benzyl-1,1-diphosphonic acid crystallizes in the form of the dihydrate. The yield is 88%.

EXAMPLE 4

On reacting an aminodiphosphonic acid having the formula

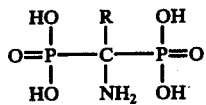

wherein R is defined in the following table, with nitrous acid, hydroxydiphosphonic acids having the formula

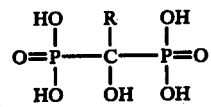

were obtained.

Specifically 50 m mols of the aminodiphosphonic acid were suspended in 60 ml water and 100 m mols of $NaNO_2$ were added slowly as a weakly acidified aqueous solution at 0° to 5° C. Subsequently the reaction mixture was stirred for one hour, then the solution was treated with an acid exchanger in the hydrogen form to replace the sodium ions. Finally the deionized reaction mixture was concentrated in the vacuum evaporator. The free acids were isolated in crystalline form. The yields are also given in the table.

TABLE

| Number | R | % Yields |
|---|---|---|
| A | CH₃—⟨phenyl⟩— | over 90% |
| B | (CH₃)(CH₃)—⟨phenyl⟩— | over 90% |
| C | C₂H₅—⟨phenyl⟩— | over 90% |
| D | Cl—⟨phenyl⟩— | over 90% |

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A process for the preparation of 1-hydroxy-alkane-1,1-diphosphonic acid of the formula

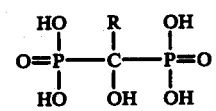

wherein R is a member having from 1 to 12 carbon atoms selected from the group consisting of alkyl having 1 to 6 carbon atoms, cyclohexyl, phenyl and phenylalkyl, all having substituents selected from the group consisting of hydrogen, methyl, ethyl, methoxy, ethoxy and halogen, consisting essentially of reacting the corresponding 1-amino-alkane-1,1-diphosphonic acid of the formula

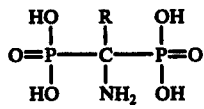

in which R has the above-assigned meaning, with at least the stoichiometric amount of aqueous nitrous acid, at a temperature between 0° and 50° C; and recovering said 1-hydroxy-alkane-1,1-diphosphonic acid.

2. The process of claim 1, in which there is from 1.2 to 2 times the molar amount of said aqueous nitrous acid.

3. The process of claim 1, wherein said aqueous nitrous acid is formed by the introduction of $N_2O_3$ into an aqueous medium of said 1-amino-alkane-1,1-diphosphonic acid.

4. The process of claim 1, wherein R is alkyl having 1 to 6 carbon atoms.

5. The process of claim 4, wherein R is methyl.

6. The process of claim 1, wherein R is a member having from 1 to 12 carbon atoms selected from cyclohexyl, phenyl and phenylalkyl, all having substituents selected from the group consisting of hydrogen, methyl, ethyl, methoxy, ethoxy and halogen.

7. The process of claim 6, wherein R is phenyl.

8. A process for the preparation of 1-hydroxy-ethane-1,1-diphosphonic acid of the formula

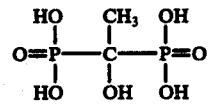

consisting essentially of reacting the corresponding 1-amino-ethane-1,1-diphosphonic acid of the formula

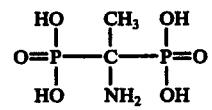

with at least the stoichiometric amount of aqueous nitrous acid, at a temperature between 0° and 50° C; and recovering said 1-hydroxy-ethane-1,1-diphosphonic acid.

* * * * *